United States Patent [19]

Kennedy et al.

[11] Patent Number: 5,211,938
[45] Date of Patent: May 18, 1993

[54] METHOD OF DETECTION OF MALIGNANT AND NON-MALIGNANT LESIONS BY PHOTOCHEMOTHERAPY OF PROTOPORPHYRIN IX PERCURSORS

[75] Inventors: James C. Kennedy; Roy H. Pottier; Robert L. Reid, all of Kingston, Canada

[73] Assignee: Queen's University at Kingston, Kingston, Canada

[21] Appl. No.: 783,750

[22] Filed: Oct. 28, 1991

Related U.S. Application Data

[63] Continuation of Ser. No. 386,414, Jul. 28, 1989, Pat. No. 5,079,262.

[51] Int. Cl.⁵ .................. G01N 33/15; A61K 31/195
[52] U.S. Cl. ...................................... 424/7.1; 514/561
[58] Field of Search ........................... 424/7.1; 514/561

[56] References Cited

U.S. PATENT DOCUMENTS 3,846,490 11/1974 Aronova et al. .................... 562/567
3,934,369 1/1976 Rebeiz ............................. 435/240.45
3,973,129 8/1976 Blumberg et al. ................. 250/461.2
4,772,681 9/1988 Fukuda et al. ....................... 540/145
4,977,177 12/1990 Bommer et al. .................... 514/410
4,997,639 3/1991 Aizawa et al. ........................ 424/9
5,043,101 8/1991 Gordon ............................ 252/408.1

FOREIGN PATENT DOCUMENTS 0233701 8/1987 European Pat. Off. .
62-63586 3/1987 Japan .
62-205081 9/1987 Japan .

Primary Examiner—Glennon H. Hollrah
Assistant Examiner—Gary E. Hollinden
Attorney, Agent, or Firm—Richard J. Hicks

[57] ABSTRACT

A method of detecting and treating malignant and non-malignant tissue abnormalities and lesions of the skin, conjunctives, respiratory, digestive and vaginal mucosa; endometrium and urothelium in which 5-aminolevulinic acid is administered to the patient in an amount sufficient to induce synthesis of protoporphyrin IX in the lesions, followed by exposure of the treated lesion to a photoactivating light in the range 350–640 nm.

2 Claims, No Drawings

METHOD OF DETECTION OF MALIGNANT AND NON-MALIGNANT LESIONS BY PHOTOCHEMOTHERAPY OF PROTOPORPHYRIN IX PERCURSORS

This application is a continuation of U.S. application Ser. No. 386 414 filed Jul. 28, 1989, now U.S. Pat. No. 5,079,262, issued Jan. 7, 1992.

FIELD OF INVENTION

This invention relates to the detection and treatment malignant) by induced fluorescence and photochemotherapy respectively.

BACKGROUND OF INVENTION

Tissue abnormalities involving the skin usually are detected and assessed by a combination of visual inspection and palpation. In certain clinical situations the sensitivity of the visual inspection can be enhanced by the use of non-white light (either ultraviolet or a narrow band in the visible), or by the prior application of a contrast-enhancing agent such as dilute acetic acid or certain stains. Tissue abnormalities that involve surfaces that cannot be palpated (such as the bronchi or the urinary bladder) may be visualized via an appropriate scope. Some specialized scopes can detect induced fluorescence. If the abnormality in question is associated with a difference in either the extend or the pattern of tissue vascularization, such a scope may be used to determine the limits of the area involved by the abnormality, by visualizing an injected bolus of fluorescein as it passes through the vasculature of both the lesion and the adjacent normal tissue.

In addition, fluorescence-detecting scopes are being used experimentally to identify areas of tissue that show strong porphyrin fluorescence following the intravenous injection of exogenous porphyrins such as hematoporphyrin IX (HpIX), hematoporphyrin derivative (HpD), or "dihematoporphyrin ether" (Photofrin II). Such porphyrins tend to accumulate semi-perferentially in malignant tissues, but they also accumulate in tissues that are regenerating following an injury or in the rapidly growing tissues of an embryo or fetus. Normal liver, spleen, and kidney also tend to accumulate these porphyrins. Using such compounds and fluorescence-detecting scopes, areas of malignant tissue too small to be identified by standard forms of visual inspection have been identified in the bronchi and in the urinary bladder.

Unfortunately, a clinically significant (photosensitizing) amount of porphyrin persists in the skin for at least two weeks, (occasionally for more than two months) following the intravenous injection of HpIX, HpD, or Photofrin II. This means that patients must avoid exposure to sunlight (either direct, or through window glass) for an annoyingly long period of time post-injection. Understandably, patient compliance often is poor, and accidental phototoxic "sunburn" is a common occurrence in the weeks following a diagnostic or therapeutic injection of porphyrin. Persistent photosensitivity is the major hazard associated with this technique, and is the main reason why it is not used more widely.

The standard or conventional forms of treatment for cancer are surgery, radiotherapy and chemotherapy. However, other forms of treatment are also known, including photochemotherapy or photodynamic therapy (PDT). PDT is currently being used, on an experimental basis, to treat several different types of cancer as well as certain nonmalignant lesions such as psoriasis. The patient is given a photo-activatable drug that has some degree of specificity for the tissue being treated. A tissue volume that includes the target tissue is then exposed to photoactivating light so as to destroy the target tissue while causing only mild and reversible damage to the other tissues in the same treatment volume.

There are two main types of photochemotherapeutic agents in clinical use at present. The first type, methoxypsoralens, are given systemically. Ultraviolet light is essential to activate them. Localized exposure of psoralen-containing tissues to ultraviolet light induces a localized photochemical reaction that causes the drug to bind covalently to the DNA of living cells, thus destroying their proliferative potential. The second type, porphyrins, are also given systemically (by intravenous injection), although occasionally they are given either topically or by intralesional injection. They can be activated by visible (red) light. The localized exposure of porphyrin-containing tissues to such light does not induce a chemical reaction between cell components and the porphyrin molecules. Instead, the porphyrins act as catalysts by trapping the energy of the photoactivating light and then passing it on to molecules of oxygen, which in turn are raised to an excited state that is capable of oxidizing adjacent molecules or structures. Cell death is not caused primarily by damage to the DNA, but by damage to essential membrane structures.

Photochemotherapy is used at present for the treatment of certain types of cancer and non-malignant lesions, including psoriasis. The goal of such treatment is sometimes cure (mainly for basal cell carcinomas), but usually the goal is palliation through local control when none of the standard forms of therapy are considered likely to offer a significant degree of benefit to the patient.

Methoxypsoralen (PUVA) therapy is used mainly for the treatment of psoriasis, but sometimes it is also used to treat very superficial cancers that involve the skin (mainly mycosis fungoides). However, there are two serious problems with such treatments. First, the procedure has been demonstrated in humans to be carcinogenic. Second, the photoactivating ultraviolet light is absorbed so strongly by most tissues that the depth at which malignant tissue can be killed is limited to a few millimeters below the illuminated surface. These problems severely limit the usefulness of the methoxypsoralens for photochemotherapy.

At present, the porphyrins most commonly used for photochemotherapy are Hematoporphyrin IX (HpIX), Hematoporphyrin derivative (HpD), and Photofrin II, a semipurified form of HpD. When porphyrins are used as photosensitizers, cell death results from damage to essential membrane structures rather than from damage to DNA. Consequently, malignant transformation is not a serious problem. Moreover, since the visible (red) light that is used to photoactivate porphyrins penetrates tissue much more deeply than does the ultraviolet light that must be used to photoactivate methoxypsoralens, the depth at which porphyrin-treated tissue can be killed is substantially greater. Also, since certain types of porphyrins show a significant tendency to accumulate preferentially in malignant tissues, it is sometimes possible to destroy malignant tissue without causing clinically significant damage to adjacent normal tissues.

The main problem with the systemic use of HpIX, HpD and Photofrin II is that photosensitizing concentrations persist in the skin for several weeks to several months following their administration. Consequently, severe accidental phototoxic skin reactions may occur unless the patient avoids exposure to sunlight (either direct, or filtered through window glass) until the concentration of the photo-sensitizer in the skin has been reduced to a harmless level. At present, the problem of photosensitivity following the administration of porphyrins is handled by advising the patient to avoid any form of exposure to sunlight (or to very bright artificial lights) for a period of at least two weeks post-injection, and to initiate subsequent exposure to sunlight very cautiously. Not all patients comply with these instructions, since it often is quite inconvenient to do so. In addition, the use of a sunscreen with a high blocking factor is recommended with a warning that this will only reduce the hazard somewhat, not eliminate it completely. In a few cases, patients whose photosensitization persisted for more than a month post-treatment have been given large daily doses of beta-carotene over a period of several months in an attempt to prevent accidental photo-toxic damage. Finally, attempts have been made to reduce phototoxicity by applying the photosensitizer topically to a limited area.

However, another type of problem is encountered if HpIX or HpD is applied topically in DMSO (Dimethylsulfoxide) Azone, or some other vehicle intended to enhance their diffusion through tissue. The porphyrins tend to become immobilized wherever they happen to be when the DMSO Azone becomes diluted by normal tissue fluids to such an extent that the porphyrins can no longer diffuse through the tissue (or even remain in solution). Consequently, the topical application of porphyrins often is associated with a loss of specificity for malignant tissues, and normal tissues near the site of application may develop persistent photosensitization from the localized concentration of porphyrin.

OBJECT OF INVENTION

It is an object of the present invention to provide a method for the detection of certain types of malignant and non-malignant tissue abnormalities by induced fluorescence.

It is another object of the present invention to provide a photodynamic (photosensitizing) treatment method which can be administrated either systemically or topically using an agent which is not in itself a photosensitizer but which induces the synthesis of protoporphyrin IX (PpIX) in vivo.

STATEMENT OF INVENTION

Thus, by one aspect of this invention there is provided a method for detecting malignant and non-malignant lesions in a patient comprising administering to said patient an effective amount of a precursor of protoporphyrin IX in the biosynthetic pathway for heme so as to induce an accumulation of protoporphyrin IX in said lesions and exposing said lesions to light having a wavelength within the absorbance spectrum of said protoporphyrin IX to thereby induce fluorescence in said lesions.

Thus, by another aspect of this invention there is provided a method for treating malignant and non-malignant hyperproliferative lesions of the skin, mucosa, endometrium and urothelium in a patient comprising administering to said patient an effective amount of a precursor of protoporphyrin IX in the biosynthetic pathway for heme so as to induce synthesis of protoporphyrin IX in said lesions, and exposing said lesions to light having a wavelength within the photoactivating action spectrum of said PpIX to thereby induce photoactivation in said lesions.

In preferred aspects of this invention the preferred precursor of protoporphyrin IX is 5-amino-4-oxo-pentanoic acid, otherwise known as 5-aminolevulinic acid, and a preferred wavelength of the photoactivating light is in the range 350–635 nm, more preferably a red light of about 635 nm.

DETAILED DESCRIPTION OF PREFERRED EMBODIMENT

Protoporphyrin IX (PpIX), a naturally occurring photosensitizer, is the immediate precursor of heme in the heme biosynthetic pathway. All nucleated cells have at least a minimal capacity to synthesize PpIX, since heme is necessary for the synthesis of various essential heme-containing enzymes. Certain types of cells and tissues can synthesize relatively large quantities of PpIX. Under normal conditions, the synthesis of PpIX in such tissues is under such tight feed-back control that the cells produce it at a rate just sufficient to match their need for heme. However, the usual rate-limiting step in the process, the synthesis of 5-aminolevulinic acid (ALA), can be bypassed by the provision of exogenous ALA, porphobilinogen, or other precursors of PpIX. Certain tissues and organs will then accumulate such a large excess of PpIX that they become both fluorescent and photosensitive. At least in the case of skin, the PpIX appears to be synthesized in situ. The ALA, which is commercially available from Sigma Chemical Company and which is water soluble, can be administered orally, topically or by injection. The oral and parenteral routes lead to the induction of clinically useful concentrations of PpIX in certain benign and malignant tissues throughout the body. Only certain types of tissue can synthesize clinically useful amounts of PpIX when provided with an excess of ALA, and the provision of ALA is only beneficial if the tissue affected is at a site that can be reached by photoactivating light. At the present time, treatment of basal cell, baso-squamous and squamous cell carcinomas and other lesions of the skin, mucosa (respiratory, digestive, and vaginal), endometrium and urothelium is contemplated. Treatment of non-malignant lesions such as genital warts and psoriasis is also contemplated. Sites could include lesions involving (i) skin and conjunctiva; (ii) the lining of the mouth, pharynx, esophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumors in solid tissues that can be made accessible to photoactivating light either directly, at time of surgery, or via an optical fibre inserted through a needle.

The wavelength of the photoactivating light is of some importance, as it has been shown that between 1 and 10 percent of incident red light (600–700 nm) can pass through a slab of human tissue 1 cm thick, whereas only 0.001 percent or less of blue light (about 400 nm) can pass through the same thickness of human tissue. The photosensitizer will, therefore, be more successful if it strongly absorbs red light. PpIX does strongly absorb red light. The present approach has several advantages over the prior art. First, PpIX has a much shorter half-life in normal tissues than does HpIX, HpD or Photofrin II. This greatly reduces the danger of accidental phototoxic skin reactions in the days following treatment. Second, the topical application of ALA to certain types of lesions can induce PpIX within those lesions, but nowhere else. This improves the specificity of the treatment, reduces the danger of accidental phototoxic reactions to a very low level, and greatly reduces the amount of both ALA and PpIX to which the entire body would be exposed if an equally effective dose of ALA were to be given systemically. Both ALA and PpIX are normal products of metabolism, and are handled quite readily by the biochemical machinery of the body. However, since very large doses of ALA (like large doses of HpIX or HpD) are associated with a transient decrease in motor nerve conduction velocity, it is desirable to reduce the dose of ALA to the minimum that is still effective. Topical application requires much less ALA than systemic administration. Third, PpIX is rapidly inactivated by the photoactivating light. Following exposure of tissues containing PpIX to a therapeutic dose of photoactivating light, there is a substantial decrease in photosensitization of the tissues within the treatment volume. Consequently, if PpIX is induced by the topical application of ALA to specific lesions, the patient can be exposed to sunlight immediately post-treatment without danger of serious phototoxicity. Fourth, ALA is an effective inducer of PpIX when given by mouth, by topical application, or by injection. In contrast, HpIX, HpD and Photofrin II are effective in most situations only when given by injection. This versatility of ALA enhances its acceptability for routine use by the medical profession, since the oral and topical routes of administration are much more convenient than the parenteral. Fifth, the normal and abnormal tissues that can be photosensitized by the administration of ALA are somewhat different from those that can be photosensitized by the administration of HpIX, HpD or Photofrin II . Consequently, ALA may be useful in clinical situations in which the other photosensitizers are not.

Thus present technique is not merely another way to do what can be done already but is, in fact, a significant advance in therapeutic capability.

EXAMPLE 1

An 87 year old patient diagnosed to have recurrent in situ squamous cell carcinoma of the right cheek and mandible was treated with a topical application of ALA 17% w/w in a Glaxal base at a dosage rate of 100 mg ALA per lesion. Two and one half hours after application the lesion was exposed to photoactivating light—the output of a 500 watt tungsten lamp, filtered to remove both infrared (heat filter) and wavelengths below 600 nm (Hoya R-60 filter) at a dose (intensity x duration) of 52.5 mWhr/cm$^2$. Forty days post treatment the patient was evaluated and the lesion was judged to have completely responded.

EXAMPLE 2

A 73 year old patient diagnosed to have in situ squamous cell carcinoma, of the right ear, upper posterior and lateral, was treated with a topical application of ALA 10% w/w in a Glaxal base at a dosage rate of 35 mg per lesion. Three hours after application of ALA, the lesion was exposed to 26 mWhr/cm$^2$ of photoactivating light from the source described in Example 1 Twenty-one day post treatment evaluation revealed complete response.

EXAMPLE 3

A 64 year old patient diagnosed to have multiple squamous cell carcinomas in:
 (1) back, left shoulder
 (2) back, right thorax
 (3) back, right thorax, lower
 (4) left hand, dorsal surface, near fingers
 (5) left hand, dorsal surface, central
 (6) left hand, near thumb joint (elevation approx. 10 mm)

had lesions 1,2 and 3 treated with 20 mg ALA per lesion in a 20% w/w Glaxal base. After three hours the lesions were exposed to photoactivating light from the source described in Example 1 at a dose of 50 Mwhr/cm$^2$. Ten days post treatment lesion 1 had an almost complete response, lesion 2 a partial response and lesion 3 a complete response. Lesions 1 and 2 and lesions 4,5 and 6 were then each treated with 22 mg ALA in a 10% w/w Glaxal base for 3 hours, followed by exposure to photoactivating light, as above at doses of:
 lesion 1 17 mWhr/cm$^2$
 lesion 2 17 mWhr/cm$^2$
 lesion 4 26 mWhr/cm$^2$
 lesion 5 26 mWhr/cm$^2$
 lesion 6 26 mWhr/cm$^2$ Twenty-five days post-treatment the patient was evaluated as follows:
 lesion 1 - complete response
 lesion 2 - complete response
 lesion 4 - no recurrence
 lesion 5 - partial response
 lesion 6 - loss of approx. 3 mm of 10 mm elevation.

EXAMPLE 4

A 43 year old patient was diagnosed to have basal cell carcinomas of (1) back, left shoulder and (2) back, high lumbar region, to right and was treated with 50 mg per lesion of ALA in a 33% w/w Glaxal base for three hours. The lesions were then photoactivated from a source as described in Example 1 at 37 mWhr/cm$^2$. 64 days post treatment, evaluation showed complete response of both lesions.

EXAMPLE 5

ALA was dissolved in isotonic saline and then administered systemically to mice by either subcutaneous or intraperitoneal injection, at a dose of 100 to 500 mg per kg of body weight. Three hours later, the mice were sacrificed and frozen sections taken of the uterus. When these sections were examined by fluorescence microscopy, the endometrium showed strong protoporphyrin fluorescence while the underlying myometrium did not. Since the ALA was administered systemically, it certainly must have been present in the myometrium, and the ensuing lack of protoporphyrin fluorescence in the myometrium must indicate that when supplied with an excess of exogenous ALA. The myometrium therefore will not become photosensitized if ALA is applied directly to the surface of the endometrium, and subsequent exposure of both the endometrium and the myometrium of the uterus to photoactivating light should result in preferential ablation of the endometrial tissue.

We claim:

1. A method for detecting malignant and non-malignant tissue abnormalities and lesions of the skin, mucosa, endometrium and urothelium in a patient, comprising administering to said patient an effective amount of a precursor of protoporphyrin IX in the biosynthetic pathway for heme so as to induce synthesis of protoporphyrin IX preferentially in said abnormalities and lesions, exposing said patient to light having a wavelength within the absorbance spectrum of said protoporphyrin IX to thereby induce fluorescence in said abnormalities or lesions, and detecting said fluorescence.

2. The method of claim 1 wherein said precursor is 5-aminolevulinic acid.

REEXAMINATION CERTIFICATE (3257th)
United States Patent [19]
Kennedy et al.

[11] B1 5,211,938
[45] Certificate Issued Jul. 8, 1997

[54] METHOD OF DETECTION OF MALIGNANT AND NON-MALIGNANT LESIONS BY PHOTOCHEMOTHERAPY OF PHOTOPORPHYRIN IX PRECURSORS

[75] Inventors: James C. Kennedy; Roy H. Pottier; Robert L. Reid, all of Kingston, Canada

[73] Assignee: Queen's University at Kingston, Kingston, Canada

Reexamination Request:
No. 90/004,476, Dec. 4, 1996

Reexamination Certificate for:
Patent No.: 5,211,938
Issued: May 18, 1993
Appl. No.: 783,750
Filed: Oct. 28, 1991

Related U.S. Application Data

[63] Continuation of Ser. No. 386,414, Jul. 28, 1989, Pat. No. 5,079,262.
[51] Int. Cl.$^6$ .............. A61B 5/06; A61K 49/00; A61K 31/40
[52] U.S. Cl. .............. 424/9.61; 514/561
[58] Field of Search .............. 424/9.61; 514/561

[56] References Cited

FOREIGN PATENT DOCUMENTS

WO91/01727  2/1996  WIPO.

OTHER PUBLICATIONS

Qian, et al. A Comparison of Different Photosensitizing Dyes with Respect to Uptake C3H-Tumors and Tissues of Mice, Cancer Letters 36:1–10 (1987).

Malik, et al. Destruction of erythroleukaemic cells by photoactivation of endogenous porphyrins, Br. J. Cancer 56:589–595 (1987).

Kennedy Photochemotherapy—Clinical Aspects Photosensitisation, NATO ASI Series H15:453–463 (1988) ed. Moreno, et al.

Fukuda, et al. Tumor–Localizing Properties of Porphyrins in vitro Studies Using the Porphyrin Precursor, Aminolevulinic Acid, in Free and Liposome Encasulated Forms, Drug Des. Deliv 5:133–139 (1989).

Malik, et al. Inactivataion of Erythrocytic, Lymphocytic and Myelocytic Leukemic Cells by Photoexcitation of Endogenous Porphyrins Journal of Photochemistry and Photobiology: Biology 4:195–205 (1989).

Divaris, et al. Phototoxic Damage to Sebaceous Glands and Hair Follicles of Mice After Systemic Administration of 5–Vol. Aminolevulinic Acid Correlates with Localized Protoporphyrin IX Fluorescence, American Journal of Pathology, 136, No. 4:891–897 (1990).

Kennedy Photodynamic Therapy with Endogenous Protoporphyrin IX: Basic Principles and Present Clinical Experience Journal of Photochemistry and Photobiology, B:Biology 6(1990) 143–148.

Kennedy, et al. Topical Photodynamic Therapy for Cancers of the Skin, Canadian Dermatology Association Journal vol. 5, No. 3:45–46 (Oct. 1991).

*Primary Examiner*—Gary E. Hollinden

[57] ABSTRACT

A method of detecting and treating malignant and non-malignant tissue abnormalities and lesions of the skin, conjuctives, respiratory, digestive and vaginal mucosa; endometrium and urothelium in which 5-aminolevulinic acid is administered to the patient in an amount sufficient to induce synthesis of protoporphyrin IX in the lesions, followed by exposure of the treated lesion to a photoactivating light in the range 350-640 nm.

B1 5,211,938

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 2 is confirmed.

* * * * *